(12) United States Patent
D'Lima et al.

(10) Patent No.: US 7,411,000 B2
(45) Date of Patent: Aug. 12, 2008

(54) PROCESS OF INHIBITING CELL DEATH IN INJURED CARTILAGE

(75) Inventors: Darryl D'Lima, San Diego, CA (US); Martin Lotz, La Jolla, CA (US); Clifford Colwell, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 235 days.

(21) Appl. No.: 10/099,408

(22) Filed: Mar. 15, 2002

(65) Prior Publication Data

US 2002/0183258 A1   Dec. 5, 2002

Related U.S. Application Data

(60) Provisional application No. 60/276,183, filed on Mar. 15, 2001.

(51) Int. Cl.
    *A01N 35/02*   (2006.01)
(52) U.S. Cl. ..................................... 514/475
(58) Field of Classification Search ................. 514/475
    See application file for complete search history.

(56) References Cited

U.S. PATENT DOCUMENTS

| | | | |
|---|---|---|---|
| 6,153,591 A * | 11/2000 | Cai et al. ....................... 514/19 |
| 6,184,210 B1 * | 2/2001 | Keana et al. ................... 514/19 |
| 6,566,338 B1 * | 5/2003 | Weber et al. ................... 514/19 |
| 2002/0055130 A1 * | 5/2002 | Johnson ...................... 435/7.21 |
| 2003/0045556 A1 * | 3/2003 | Ghosh et al. ................. 514/357 |

OTHER PUBLICATIONS

The Merck Manual of Diagnosis and Therapy, 16th Edition, 1992 (Merck Research Labs: Rahway, NJ), p. 1305-1307.*
Lozoya et al. "A novel rate osteoarthrosis model to assess apoptosis and matrix degradation" Pathology, Research and Practice (2000) 196(11): 729-45.*
"Modern Pharmacology" Craig et al., Ed. (1990) (Little, Brown and Co.: Boston), p. 82-83.*
Li et al. "Functional role and therapeutic implications of neuronal caspase-1 and -3 in a mouse model of traumatic spinal cord injury" Neurosci. (200).99(2): 333-342.*
Emery et al. "Apoptosis after traumetic human spinal cord injury" J. Neurosurg. (1998) 89: 911-920.*
Starr et al. Biology: The unity and Diversity of life. (Wadsworth Publishing Company: Belmont, CA)(1987) p. 331.*
Taber's Cyclopedic Medical Dictional. Thoams, editor. 15th edition. (F.A. Davis Company: Philadelphia, PA) (1985) pp. 1846-1849.*
Horten, et al., "Chondrocyte Apoptosis in Development, Aging and Disease", *Matrix Biol. 17*: 107-115 (1998).
Hashimoto, et al., "Chondrocyte-derived apoptotic bodies and calcification of articular cartilage", *Proc. Natl. Acad. Sci. USA 95*: 3094-3099 (1998).
Muzio, et al., "An Induced Proximity Model for Caspase-8 Activation", *J. Biol. Chem. 273*: 2926-2930 (1998).
Martin, et al., "Membrane Oligomerization and Cleavage Activates the Caspase-8 (FLICE/MACHα1) Death Signal", *J. Biol. Chem. 273*: 4345-4349 (1998).
Hirata, et al., "Caspases Are Activated in a Branched Protease Cascade and Control Distinct Downstream Processes in Fas-induced Apoptosis", *J. Exp. Med. 187*: 587-600 (1998).
Hashimoto, et al., "Chondrocyte Apoptosis and Nitric Oxide Production During Experimentally Induced Osteoarthritis", *Arth. Rheum. 41*: 1266-1274 (1998).
Kroemer, "Mitochondrial control of apoptosis: an overview", *Biochem. Soc. Symp. 66*: 1-15 (1999).
Quinn, et al., "Physical and Biological Regulation of Proteoglycan Turnover around Chondrocytes in Cartilage Explants: Implications for Tissue Degradation and Repair", *Ann. N.Y. Acad. Sci. 878*: 420-441 (1999).
Elkon, K. B., "Caspases: Multifunctional Proteases", *J. Exp. Med. 190*: 1725-1727 (1999).
Kuida, K., "Caspase-9", *Int. J. Biochem. Cell Biol. 32*: 121-124 (2000).
Tew, et al., "The Reactions of Articular Cartilage to Experimental Wounding", *Arth. Rheum. 43*: 215-225 (2000).
Nuttall, et al., "Inhibition of Caspase-3-like Activity Prevents Apoptosis while Retaining Functionality of Human Chondrocytes In Vitro", *J. Orthop. Res. 18*: 356-363 (2000).
Pelletier, et al., "Selective Inhibition of Inducible Nitric Oxide Synthase Reduces Progression of Experimental Osteoarthritis In Vivo: Possible Link with the Reduction in Chondrocyte Apoptosis and Caspase 3 Level", *Arth. Rheum. 43*: 1290-1299 (2000).
Loening, et al., "Injurious Mechanical Compression of Bovine Articular Cartilage Induces Chondrocyte Apoptosis", *Arch. Biochem. Biophys. 381*: 205-212 (2000).
Lee, et al., "Potent and Selective Nonpeptide Inhibitors of Caspases 3 and 7 Inhibit Apoptosis and Maintain Cell Functionality", *J. Biol. Chem. 275*: 16007-16014 (2000).
Nakagawa, et al., "Caspase-12 mediates endoplasmic-reticulum-specific apoptosis and cytotoxicity by amyloid-β", *Nature 403*: 98-103 (2000).

(Continued)

*Primary Examiner*—Sandra Saucier
*Assistant Examiner*—Susan Hanley
(74) *Attorney, Agent, or Firm*—Schwegman, Lundberg & Woessner, P.A.

(57) ABSTRACT

Processes for inhibiting apoptotic cell death and glycosaminoglycan release from injured cartilage is provided. Inhibition is accomplished using caspase inhibitors.

8 Claims, No Drawings

OTHER PUBLICATIONS

Woolley, D. E., et al., "Observations on the microenvironmental nature of cartilage degradation in rheumatoid arthritis", *Ann Rheum Dis.*,56(3), (Mar. 1997), pp. 151-161.

Ghosh, Peter, *The Biology of the Intervertebral Disc*, Boca Raton, Fla.:CRC Press (1988), pp. 1-37.

Inoue, H., "Three-dimensional architecture of lumbar intervertebral discs.", *Spine*, 6(2) (Mar.-Apr. 1981), pp. 139-146.

Bae, S., et al., "Role of caspase-independent apoptosis in cardiovascular diseases", *Frontiers in Bioscience*, vol. 13,(Jan. 1, 2008),pp. 2495-2503.

Clements, K., et al., "The spread of cell death from impact damaged cartilage: lack of evidence for the role of nitric oxide and caspases", *OsteoArthritis and Cartilage*, vol. 12,(2004),pp. 577-585.

D'Lima, D., et al., "Caspase inhibitors reduce severity of cartilage lesions in experimental osteoarthritis", *Arthritis & Rheumatism*, vol. 54, No. 6,(Jun. 2006),pp. 1814-1821.

Kurz, B., et al., "Influence of tissue maturation and antioxidants on the apoptotic response of articular cartilage after injurious compression", *Arthritis & Rheumatism*, vol. 50, No. 1,(Jan. 2004),pp. 123-130.

Moore, R. J., "The vertebral endplate: disc degeneration, disc regeneration.", *Eur Spine J.*, 15 Suppl 3, (Aug. 2006),S333-7.

Rothenfluh, Dominique A., et al., "Biofunctional polymer nanoparticles for intra-articular targeting and retention in cartilage", *Nature Materials, Published online*: Feb. 3, 2008, (2008),7 pgs.

Roughley, P. J., "Biology of intervertebral disc aging and degeneration: involvement of the extracellular matrix.", *Spine*, 29(23), (Dec. 1, 2004),2691-9.

Tewari, M., et al., "Diagnosis and prognostication of adult spinal cord injury without radiographic abnormality using magnetic resonance imaging: analysis of 40 patients", *Surgical Neurology*, vol. 63,(2005),pp. 204-209.

\* cited by examiner

SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: N-carbobenzyloxy residue
<220> FEATURE:
<221> NAME/KEY: MOD_RES
<222> LOCATION: 4
<223> OTHER INFORMATION: Methyl ester on the side chain, fluormethyl ketone makes up the C-terminus

<400> SEQUENCE: 1

Tyr Val Ala Asp
 1

<210> SEQ ID NO 2
<211> LENGTH: 5
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: N-carbobenzyloxy carbamate protection on the
      N-terminus
<220> FEATURE:
<221> NAME/KEY: MOD_RES
<222> LOCATION: 5
<223> OTHER INFORMATION: Methyl protection of the carboxylic acid on the
      side chain; C-terminus is a fluoro-
      methyl ketone with the C-1 carbon of aspartyl
      being the carbonyl carbon

<400> SEQUENCE: 2

Val Asp Val Ala Asp
 1               5

<210> SEQ ID NO 3
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: N-carbobenzyloxy protection of the N-terminal
      amine
<220> FEATURE:
<221> NAME/KEY: MOD_RES
<222> LOCATION: 4
<223> OTHER INFORMATION: methyl ester protection of the carboxylic acid
      side chain;
      C-terminus is a fluoromethyl
      ketone with the C-1 carbon of the aspartyl residue
      being the carbonyl carbon of the ketone

<400> SEQUENCE: 3

Asp Glu Val Asp
 1

<210> SEQ ID NO 4
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: N-Carbobenzyloxy group at the N-terminus
<220> FEATURE:
<221> NAME/KEY: MOD_RES
<222> LOCATION: 4
<223> OTHER INFORMATION: Methyl ester protection of the carboxylic acid
      side chain;
      C-terminal fluoromethyl ketone where the C-1
      carbon of the

```
      aspartyl residue is the carbonyl carbon of the
      ketone

<400> SEQUENCE: 4

Leu Glu Val Asp
 1

<210> SEQ ID NO 5
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protected N-terminal amine; Cbz
      group
<220> FEATURE:
<221> NAME/KEY: MOD_RES
<222> LOCATION: 4
<223> OTHER INFORMATION: Methyl ester protection of the carboxylic acid
      side chain;
      C-terminal fluoromethyl ketone
      where the C-1 carbon of the aspartyl residue is
      the carbonyl carbon of the ketone

<400> SEQUENCE: 5

Trp Glu His Asp
 1

<210> SEQ ID NO 6
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protection of the N-terminal
      amine
<220> FEATURE:
<221> NAME/KEY: MOD_RES
<222> LOCATION: 4
<223> OTHER INFORMATION: Methyl ester protection of the carboxylic acid
      side chain;
      C-terminal fluoromethyl ketone where the C-1
      carbon of the aspartyl residue is the carbonyl
      carbon of the ketone

<400> SEQUENCE: 6

Val Glu Ile Asp
 1

<210> SEQ ID NO 7
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protection of the N-terminal
      amino group
<220> FEATURE:
<221> NAME/KEY: MOD_RES
<222> LOCATION: 4
<223> OTHER INFORMATION: Methyl ester protection of the carboxylic acid
```

```
          side chain;
          C-terminal fluoromethyl ketone where the C-1
          carbon of the aspartyl residue is the carbonyl
          carbon of the ketone

<400> SEQUENCE: 7

Ile Glu Thr Asp
1

<210> SEQ ID NO 8
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protection of the N-terminal
      amine
<220> FEATURE:
<221> NAME/KEY: MOD_RES
<222> LOCATION: 4
<223> OTHER INFORMATION: Methyl ester protection of the carboxylic acid
      side chain;
      C-terminal fluoromethyl ketone where the C-1
      carbon of the aspartyl residue is the carbonyl
      carbon of the ketone

<400> SEQUENCE: 8

Leu Glu His Asp
1

<210> SEQ ID NO 9
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protection of the N-terminal
      amino group
<220> FEATURE:
<221> NAME/KEY: MOD_RES
<222> LOCATION: 4
<223> OTHER INFORMATION: Methyl ester protection of the carboxylic acid
      side chain;
      C-terminal fluoromethyl ketone where the C-1
      carbon of the aspartyl residue is the carbonyl
      carbon of the ketone

<400> SEQUENCE: 9

Ala Glu Val Asp
1

<210> SEQ ID NO 10
<211> LENGTH: 4
<212> TYPE: PRT
<213> ORGANISM: Artificial Sequence
<220> FEATURE:
<223> OTHER INFORMATION: caspase inhibitor; fluoromethyl ketone on the
      C-terminus
<220> FEATURE:
<221> NAME/KEY: MOD_RES
<222> LOCATION: 1
<223> OTHER INFORMATION: Carbobenzyloxy protection of the N-terminal
      amino group
<220> FEATURE:
<221> NAME/KEY: MOD_RES
```

```
<222> LOCATION: 4
<223> OTHER INFORMATION: Methyl ester protection of the carboxylic acid
      side chain;
      C-terminal fluoromethyl ketone where the C-1
      carbon of the aspartyl residue is the carbonyl
      carbon of the ketone

<400> SEQUENCE: 10

Leu Glu Glu Asp
 1
```

PROCESS OF INHIBITING CELL DEATH IN INJURED CARTILAGE

CROSS-REFERENCE TO RELATED APPLICATION

This application is a continuation of U.S. patent application Ser. No. 60/276,183, filed Mar. 15, 2001, incorporated herein by reference.

Funds used to support some of the studies reported herein were provided by the United States Government (NIH Grant AG07996). The United States Government, therefore, has certain rights in this invention.

TECHNICAL FIELD OF THE INVENTION

The field of this invention is cartilage injury. More particularly, the present invention pertains to a process for inhibiting apoptotic cell death and glycosaminoglycan release in mechanically injured cartilage using caspase inhibitors.

BACKGROUND OF THE INVENTION

Articular cartilage has poor reparative potential, but the reasons for this are not fully understood (Archer (1994) *Ann. Rheum. Dis.* 53, 624-630, Silver, et al. (1993) *Otolaryngol. Clin. North Am.* 28, 847-864). The lack of tissue vascularization and the putative absence of stem cells are potential explanations. Although histologic studies demonstrate the occurrence of chondrocyte death in response to mechanical injury, it is not fully known which stimuli trigger cell death and whether cell death occurs as apoptosis or necrosis (Calandruccio, et al. (1962) *J. Bone Joint Surg. Am.* 44A, 431-455, Mankin (1962) *J. Bone Joint Surg. Am.* 44A, 682-688, Bentley, et al. (1971) *Nature* 230, 385-388, Repo, et al. (1977) *J. Bone Joint Surg. Am.* 59A, 1068-1076). Cartilage, unlike other tissues, has no means of removing dead cells by phagocytosis due to the absence of tissue macrophages. Consequently, it may be proposed that lesions containing apoptotic or necrotic cells are detrimental, partly explaining poor integration with surrounding articular cartilage which is a common feature of most reported repair models. However, where this zone of cell death was resorbed by added macrophages, full repair has been reported (Joseph, et al. (1961) *J. Anat.* 95, 564-568).

Similarly, in marginal regions of injured meniscus where cell death was not observed, repair can be complete (Walmsley, et al. (1938) *J. Anat.* 12, 260-263). Collectively, these findings suggest that chondrocyte death may be one of the limiting factors in the response of cartilage to injury. However, information on the induction of cell death in response to mechanical injury is limited. It has recently been proposed that cell death in response to wounding is a combination of necrosis and apoptosis (Tew, et al. (2000) *Arthritis Rheum.* 43, 215-225). This distinction may be critical since apoptosis can be inhibited resulting in a potential increase in cell viability. Apoptosis has been inhibited in various settings (Rudel (1999) *Herz.* 124, 236-241).

Joint loading and motion can induce a wide range of metabolic responses in cartilage. Immobilization or reduced loading leads to a decrease in glycosaminoglycan (GAG) synthesis and content (Caterson, et al. (1978) *Biochim. Biophys. Acta.* 540, 412-422, Kiviranta, et al. (1987) *Arthritis Rheum.* 30, 801-809, Guilak (1994) *J. Microsc.* 173, 245-256, Sah, et al. (1989) *J. Orthop. Res.* 7, 619-636, Burton-Wurster, et al. (1993) *J. Orthop. Res.* 11, 717-729, Kim, et al. (1994) *Arch. Biochem. Biophys.* 311, 1-12). Increased dynamic loading causes an increase in GAG synthesis and content (Caterson, et al. (1978) *Biochim. Biophys. Acta.* 540, 412-422, Kirviranta, et al. (1987) *Arthritis Rheum.* 30, 801-809, Sah, et al. (1989) *J. Orthop. Res.* 7, 619-636, Gray, et al. (1988) *J. Orthop. Res.* 6, 777-792, Jones, et al. (1982) *Clin. Orthop.* 165, 283-289, Sah, et al. (1991) *Arch. Biochem. Biophys.* 286, 20-29). More severe static or impact loading causes cartilage deterioration and leads to osteoarthritic changes (Repo, et al. (1977) *J. Bone Joint Surg. Am.* 58A, 1068-1076, Gritzka, et al., *J. Bone Joint Surg. Am.* 55A, 1698-1720, Radin, et al. (1984) *J. Orthop Res.* 2, 221-234, Thompson, et al. (1991) *J. Bone Joint Surg. Am.* 73A, 990-1001). In fact, traumatic cartilage injury represents a major risk factor for the development of secondary osteoarthritis.

Prior histologic studies have demonstrated the occurrence of cell death after articular cartilage injury (Calandruccio, et al. (1962) *J. Bone Joint Surg. Am.* 44A, 431-455, Mankin (1962) *J. Bone Joint Surg. Am.* 44A, 682-688). More recently, cell death in response to articular cartilage wounding has been reported (Tew, et al. (2000) *Arthritis Rheum.* 43, 215-225). Electron microscopy and TUNEL evidence of both necrosis and apoptosis was seen in a band along the would margins. An increase in the band of cell death was observed over the first 5 days following the wounding. These phenomena were demonstrated in explants from bovine metacarpal and metatarsal joints with the production of a manually created cartilage defect. Clinically, accidental blunt trauma is by far the more common form of injury leading to cartilage lesions. Articular cartilage can sustain injury without apparent loss of matrix. It is possible that cell death (whether apoptotic or necrotic) may occur giving rise to later matrix degradation and the subsequent development of a full thickness cartilage lesion. Another recent study by Loening et al. demonstrated apoptosis after a similar injurious loading of cartilage explants (Loening, et al. (2000) *Arch. Biochem. Biophys.* 381, 205-212). Recently, broad spectrum caspase inhibitors and selective non-peptide caspase inhibitors have been successfully used to inhibit apoptosis induced by several agents in cultured human chondrocytes (Lee, et al. (2000) *J. Biol. Chem.* 275, 16007-16014, Nuttal, et al., (2000) *J. Orthop. Res.* 18, 356-363). In the setting of mature articular cartilage with a limited source of chondrocytes, maintaining viability could substantially impact subsequent degeneration and repair.

The experimental models used in most prior studies are not especially useful in predicting clinical outcomes. There is a need therefore for clinically relevant studies disclosing the mechanisms underlying cell death in injured cartilage. The model used in the current study was chosen to represent a type of blunt trauma that is more clinically relevant.

BRIEF SUMMARY OF THE INVENTION

The present invention provides a process of inhibiting apoptotic cell death in cartilage following mechanical injury. The process includes the step of inhibiting the activity of cysteine-aspartate-specific proteases in the injured cartilage. Preferably, the activity of cysteine-aspartate-specific proteases is inhibited by contacting the cartilage with an inhibitor of cysteine-aspartate-specific proteases. An especially preferred such inhibitor is a broad based inhibitor of cysteine-aspartate-specific proteases. One especially preferred such inhibitor is a fluoromethylketone caspase inhibitor such as benzyloxy-carbonyl-Val-Ala-Asp (OMe) fluoromethylketone. In another aspect, this invention provides a process of inhibiting glycosaminoglycan (GAG) release from cartilage following mechanical injury of the cartilage, wherein the process includes the step of inhibiting apoptotic cell death in the injured cartilage.

DETAILED DESCRIPTION OF THE INVENTION

The present invention provides processes for inhibiting apoptotic cell death and GAG release from cartilage following mechanical injury. The processes include the step of inhibiting, in the injured cartilage, the activity of cysteine-aspartate-specific proteases. Apoptosis is mediated by a cascade of aspartate-specific cysteine proteases or caspases (Rudel (1999) *Herz.* 24, 236-241). The family of cysteine aspartate-specific proteases (caspases) are mediators of cell death. Caspases cleave structural proteins, and regulators of transcription, DNA replication, DNA/RNA metabolism, and DNA degradation (Nuttall, et al. (2000) *J. Orthop. Res.* 18, 356-363, Elkon (1999) *J. Exp. Med.* 190, 1725-1728). Caspase-8 has been shown to play a central role in signal transduction downstream of cell membrane death receptors (Martin, et al. (1998) *J. Biol. Chem.* 273, 4345-4349, Muzio, et al. (1998) *J. Biol. Chem.* 273, 2926-2930). In this pathway, caspase-8 activates caspases-3 and -7, while caspase-3 activates caspase-6. Caspases-3 and -6 cleave proteins leading to nuclear apoptosis (Hirata, et al., (1998) *J. Exp. Med.* 187, 587-600). Mitochondria have also been implicated in apoptosis. One of the first events detected is a drop in the mitochondrial transport membrane potential. This is associated with release of cytochrome c into the cytoplasm which results in activation of caspase-9 (Kroemer (1999) *Biochem. Soc. Symp.* 66, 1-15, Kuida (2000) *Int. J. Biochem. Cell Biol.* 32, 121-124). More recently, caspase-12 has been implicated in apoptosis resulting from stress in the endoplasmic reticulum (Nakagawa, et al. (2000) *Nature* 403, 98-103). Caspases therefore appear to be the downstream executors in almost all forms of apoptosis. In accordance with the present invention, therefore, cysteine-aspartate-specific protease activity is preferably inhibited through the use of caspase inhibitors, as are well known in the art. Exemplary caspase inhibitors are shown in Table 1, below. Broad spectrum caspase inhibition can be accomplished using a variety of fluormethylketones. An exemplary and preferred such fluormethylketone is benzyloxycarbonyl-Val-Ala-Asp-(OMe) fluoromethyl ketone.

TABLE 1

| Caspase-1 Inhibitor: | YVAD-FMK | (SEQ ID NO 1) |
| Caspase-2 Inhibitor: | VDVAD-FMK | (SEQ ID NO 2) |
| Caspase-3 Inhibitor: | DEVD-FMK | (SEQ ID NO 3) |
| Caspase-4 Inhibitor: | LEVD-FMK | (SEQ ID NO 4) |
| Caspase-5 Inhibitor: | WEHD-FMK | (SEQ ID NO 5) |
| Caspase-6 Inhibitor: | VEID-FMK | (SEQ ID NO 6) |
| Caspase-8 Inhibitor: | IETD-FMK | (SEQ ID NO 7) |
| Caspase-9 Inhibitor: | LEHD-FMK | (SEQ ID NO 8) |
| Caspase-10 Inhibitor: | AEVD-FMK | (SEQ ID NO 9) |
| Caspase-13 Inhibitor: | LEED-FMK | (SEQ ID NO 10) |

Y = Tyr
L = Leu
V = Val
W = Trp
A = Ala
I = Ile
D = Asp
T = Thr
E = Glu
H = His

Inhibition of caspase activity in cartilage is accomplished by exposing the cartilage to an effective caspase inhibitory amount of the inhibitor. Exposing is accomplished by providing an effective amount of the inhibitor in fluid bathing or perfusing the cartilage. Where the cartilage is situated in vitro or in situ, the effective amount of the inhibitor is added to the medium bathing or surrounding the cartilage. The cartilage is then maintained in that medium for a period of time sufficient for caspase inhibition. Suitable media for maintaining cartilage in vitro or in situ are well known in the art.

There is dose response relationship between the amount of inhibitor and the inhibition of apoptotic cell death and GAG release. Thus, a preferred effective amount of a caspase inhibitor is from about 20 µm to about 250 µm. More preferably, the inhibitor is present in an amount of from about 50 µm to about 150 µm. Where the cartilage is situated in vivo, the inhibitor is systemically administered as to achieve effective levels in the blood and interstitial fluid perfusing the cartilage. One of skill in the art can readily calculate the amount of inhibitor needed to achieve such levels.

In another aspect, the present invention provides a pharmaceutical composition comprising a therapeutically effective amount of a caspase inhibitor in combination with a pharmaceutically acceptable carrier. As used herein, the terms "pharmaceutically acceptable", "physiologically tolerable" and grammatical variations thereof, as they refer to compositions, carriers, diluents and reagents, are used interchangeable and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Cartilage explants obtained from bovine and human bone were subjected to a variety of mechanical load injuries (See the Examples hereinafter). The release of GAG from injured cartilage and the extent of apoptosis in the injured cartilage was determined. GAG release was measured to determine if this was dose related and occurred in a time dependent manner.

In bovine cartilage, GAG release (expressed as a percent of total GAG content of the explant) increased with intensity of loading at 48 hours after loading. There was no significant difference between GAG release of Control (mean 1%, SD±0.7) and Low Load explants (mean 3%, SD±0.8). However, both the Moderate Load (mean 4%, SD±0.3) and High Load (mean 19%, SD±18.9) explants demonstrated a higher level of GAG release compared with Control ($p<0.02$). A few explants in the High Load group suffered structural damage and released much higher levels of GAG than others. When analyzed separately (undamaged vs. damaged), the High Load-damaged group demonstrated significantly higher GAG release rates than High Load-undamaged group ($p<0.01$). In the time course series, GAG release was consistently higher for the loaded explants at all the time points tested.

In human cartilage, GAG release (expressed as a percent of total GAG content of control explants) increased significantly with injury at 96 hours after loading. Loaded explants (mean 1.9%, SD±0.14) demonstrated a higher level of GAG release compared with Control (mean 0.8%, SD±0.28) ($p<0.02$). This was also confirmed by Safranin-O staining of histological sections which showed reduced intensity of stain from the upper one-third to one-half of the loaded cartilage sections.

The extent of apoptosis was studied to establish whether chondrocyte apoptosis occurs in response to mechanical injury and to determine the response to different load magnitudes. In bovine cartilage, at 48 hours, control explants demonstrated mean baseline apoptosis of 18% (0-30%). Low Load explants did not demonstrate any significant difference at mean 15% (0-30%). Both Moderate Load and High Load explants exhibited significantly higher apoptosis rates at 40% (range, 22-48%) and 47% (range, 28-60%) respectively ($p<0.01$). The time course experiments demonstrate that the percentage of apoptotic cells increases in a time-dependent manner up to 48 hours after injury. In addition, a correlation of GAG release with apoptosis rate was noted ($r=0.67$, $p<0.01$). Control explants demonstrated fewer apoptotic cells which were located mainly in the superficial zone, while High Load explants revealed apoptotic cells in superficial and intermediate zones with very few in the deep zone. Explants treated with sodium nitroprusside demonstrated a widespread pattern of apoptosis. Confirmation that chondrocytes were indeed undergoing apoptosis was obtained by electron microscopy. No significant increase in the incidence of apoptosis was seen at the cut edges of the explants between control and loaded explants.

In human cartilage, explants were examined by TUNEL to determine if chondrocyte apoptosis does occur in response to mechanical injury. At 96 hours, Control explants demonstrated mean baseline apoptosis of 4% (SD±2). Loaded implants (stress level=14 MPa) exhibited significantly higher apoptosis rates, mean 34% (SD±11, $p<0.01$). Control explants demonstrated a few apoptotic cells which were located mainly in the superficial zone, while loaded explants revealed apoptotic cells in superficial and intermediate zones. The deep zones consistently demonstrated minimal or no apoptosis. Electron microscopy revealed apoptotic chondrocytes in the loaded explants but none in the control explants. Immunohistochemical staining with the M30 monoclonal antibody also confirmed results obtained by TUNEL in the samples tested. No significant increase in the incidence of apoptosis was seen at the cut edges of the explants in either control or loaded explants suggesting that the explant harvesting procedure did not induce significant apoptosis. In both bovine and human cartilage, there was a significant correlation of GAG release with apoptosis rate.

Apoptosis is known to occur after an ordered sequence of cellular events. Although apoptosis can be induced by several different triggers, it is characteristically associated with the sequential activation of caspases. The time course of apoptosis is therefore of particular significance as it would determine the presence or absence of a therapeutic window for potential modulation of the apoptotic process. Two series of experiments were performed to determine the time course of apoptosis after mechanical injury. The first set of experiments demonstrated no significant increase in the percentage of apoptotic cells up to 6 hours after injury. The percentage of cells undergoing apoptosis increased from 6 hours after injury to 96 hours after injury. In the second set of experiments, wider time intervals were used and the percentage of apoptosis was found to continue to increase up to 7 days after injury.

The results demonstrate that cartilage mechanical injury in vitro can result in chondrocyte apoptosis within the range of load intensities tested. Apoptosis appears to be dose related and increases with increasing loads. The percentage of cells undergoing apoptosis was measured by TUNEL and confirmed by electron microscopy. The distribution of TUNEL positive cells was consistent within groups. Control explants demonstrated a few scattered apoptotic cells in the superficial zone, while higher load explants showed more apoptotic cells in the superficial and intermediate zones, with very few in the deeper zones. This increase in the percentage of apoptotic cells found close to the articular surface shows that superficial cells are more susceptible than deeper cells.

The demonstration of load induced apoptosis in cartilage also has implications for the pharmacologic modulation of post-traumatic cartilage lesions. The present study also demonstrated that caspase inhibition reduces chondrocyte apoptosis after mechanical injury. Thus, following mechanical injury to cartilage, there is likely a time period during which chondrocyte apoptosis is sensitive to pharmacologic inhibition. This has not been observed in a previous report of cartilage injury (Tew, et al. (2000) *Arthritis Rheum.* 43, 215-225).

Proteoglycan release has previously been used as a measure to estimate the extent of mechanical injury. In the present study there was a clear dose dependent release of proteoglycan in response to the intensity of load. This validates that in vitro loading (at 14 and 23 MPa) produces a reproducible metabolic response indicative of cartilage injury. Quinn et al. reported an increase in cell-mediated matrix catabolic processes with increased rates of proteoglycan turnover following cartilage injury that may explain the increased loss of GAG in media (Quinn, et al. (1999) *Ann. N. Y Acad. Sci.* 878, 420-441). More recently, Lee et al., reported that apoptosis prevention restored type II collagen promoter activity in chondrocytes (Lee, et al. (2000) *J. Biol. Chem.* 275, 16007-16014). In the present study, inhibition of chondrocyte apoptosis was associated with a reduction in proteoglycan depletion. This shows that cell death even in the form of apoptosis is likely linked to matrix loss in cartilage. Both apoptosis and proteoglycan release correlated with load intensity and with each other, suggesting a possible link between apoptosis and matrix loss after mechanical injury.

The contribution of cell death to cartilage degradation has been previously suggested for human and experimentally induced osteoarthritis (Hashimoto, et al. (1998) *Proc. Natl. Acad. Sci. USA* 95, 3094-3099, Hashimoto, et al. (1998) *Arthritis Rheum.* 41, 1266-1274, Horton, et al. (1998) *Matrix Biol.* 17, 107-115). In these cartilage pathologies, a close correlation between the frequency of chondrocyte apoptosis and severity of osteoarthritic changes was seen. Possible mechanisms are the presence and release of active enzymes that cause matrix calcification or degradation from apoptotic bodies (Hashimoto, et al. (1998) *Proc. Natl. Acad. Sci. USA* 95, 3094-3099). A correlation has been found between the level of nitric oxide production, chondrocyte apoptosis and matrix depletion in a rabbit model of osteoarthritis (Hashimoto, et al. (1998) *Arthritis Rheum.* 41, 1266-1274). More recently, Pelletier et al., reported on a reduction of the severity of experimental canine osteoarthritis, chondrocyte apoptosis, and caspase 3 activity, after treatment with a selective inhibitor of inducible nitric oxide syntheses (Pelletier, et al. (2000) *Arthritis Rheum.* 43, 1290-1299). The inhibition of apoptosis as a therapeutic modality may therefore have an even more far reaching impact on osteoarthritis than the initial preservation of cell viability.

The present disclosure shows that in vitro loading at selected injury levels, produces reproducible metabolic response indicative of cartilage injury. More severe static or impact loading causes cartilage deterioration and leads to osteoarthritic changes. The present results also show that cartilage mechanical injury results in chondrocyte apoptosis at the load intensities used. The percentage of cells undergoing apoptosis was measured by TUNEL and confirmed using two other methods: electron microscopy and immunohistochemical staining with M30. Electron microscopy of loaded samples demonstrated cellular patterns characteristic of apoptosis. An early feature of apoptosis is the cleavage of cytokeratin 18 by caspases. This exposes a neo-epitope specific for apoptosis which can be detected by M30, a monoclonal antibody. Cells staining positive for this neo-epitope was found mainly in loaded samples confirming TUNEL results.

Cell death, even in the form of apoptosis appears to be linked to matrix degradation in cartilage. Since cartilage does not contain tissue macrophages, there is no apparent mechanism for removing dead cells or apoptotic bodies. This raises the possibility that chondrocyte apoptotic remnants could cause further tissue damage and impact subsequent repair. The present demonstration of a distinct time course of load induced apoptosis in cartilage therefore has application for the pharmacologic modulation of posttraumatic cartilage lesions. Results of this study show that broad spectrum caspase inhibition can prevent chondrocyte apoptosis in vitro after mechanical injury.

In conclusion, chondrocyte apoptosis can be induced by mechanical injury in vitro in a dose dependent manner. Apoptosis induced by mechanical injury in vitro can be reduced by caspase inhibition. Caspase inhibition also reduces the proteoglycan depletion produced by mechanical injury.

EXAMPLE 1

Bovine Cartilage Studies

Cartilage Explants.

Macroscopically normal weight bearing portions of freshly slaughtered skeletally mature bovine femoral condyles were selected from animals between 2 and 6 years of age (Animal Technologies, Austin, Tex.). Only joints without visible signs of degeneration or aging were selected. Using sterile techniques, fall thickness cartilage was separated from underlying subchondral bone with a scalpel and 5 mm diameter cylindrical explants, ranging from 1 to 1.8 mm in height, cored out using a dermal punch (Acuderm, Inc., Ft. Lauderdale, Fla.). Explants taken from adjacent sites were used as matched controls for each group in each experiment to minimize variation in cartilage response due to differences in thickness and location within the joint. Each explant was weighed and allowed to stabilize at 37° C. and 5% $CO_2$ for 48 hours in 1 ml of Dulbecco's modified Eagle's medium (DMEM) supplemented with 10% fetal bovine serum (FBS), L-glutamine, antibiotics and 50 µg/ml ascorbic acid.

Full thickness bovine cartilage explants, 5 mm in diameter, were subjected to a single static mechanical load of 7, 14 or 23 MPa for 500 msec. This model simulates traumatic cartilage injury and the loads were similar in magnitude to those generated during traumatic joint injury. Glycosaminoglycan (GAG) release and percent apoptotic cells were measured. The effect of a pan-caspase inhibitor, z-VAD.fmk [benzyloxycarbonyl-Val-Ala-Asp (OMe) fluoromethylketone] in preventing chondrocyte apoptosis was determined. z-VAD-.fmk is a fluoromethylketone irreversible inhibitor of a broad spectrum of caspases. A significant increase in the number of apoptotic cells was observed in response to mechanical loading at 14 and 23 MPa when compared with control. The percentage of apoptotic chondrocytes was related to load intensity and correlated with the level of GAG release from cartilage. The pan-caspase inhibitor reduced chondrocyte apoptosis after mechanical injury. This was also associated with a reduction in GAG release. These results demonstrate that mechanical injury induces chondrocyte apoptosis which is sensitive to pharmacologic inhibition. This identifies a new approach to limit traumatic cartilage injury and the subsequent development of secondary osteoarthritis.

Loading Apparatus and Procedure.

A model to simulate acute joint injury was used in this study based on injury models reported by Repo and Finlay, and Jeffrey et al. (Repo, et al. (1977) *J. Bone Joint Surg. Am.* 59A, 1068-1076, Jeffrey, et al. (1995) *Arch. Biochem. Biophys.* 322, 87-96). Although these reported models impacted cartilage using drop towers, a more controlled method was chosen for applying and maintaining stress or strain as follows. An Instron 8511 servohydraulic testing machine (Instron Corporation, Boston, Mass.) was used to mechanically load the cartilage explants. Explants were transported from the incubator to the Instron machine in sealed cell culture dishes. The explant was centralized on a stainless steel loading platform and a radially unconfined compressive load was applied through an impermeable stainless steel platen. A small preload (0.1 MPa) was applied for 2 minutes, followed by a single 500 msec trapezoidal loading waveform at the selected stress. The stress rose from 0.1 MPa to the chosen stress level in 100 msec and was maintained for 500 msec. Three stress levels were chosen to represent acute joint injury. 7 MPa has been reported to be the upper limit of physiologic stress developed during activities of daily living (von Eisenhart, et al. (1999) *J. Orthop. Res.* 17, 532-539). 23 MPa is the stress above which the underlying bone has been reported to fracture (Haut (1989) *J. Orthop. Res.* 7, 272-280). Control explants were placed in the loading apparatus but not loaded. Both control and loaded explants were re-cultured in fresh culture media immediately after loading. Stress and strain data were recorded during the test.

Dose Response.

To establish extent of tissue response to mechanical injury three stress levels were selected: Low Load (7 MPa), Moderate Load (14 MPa) and High Load (23 MPa). Prior pilot tests demonstrated that loads below 7 MPa did not result in any measurable cell death and loads above 23 MPa resulted in extensive structural damage of the tissue. The range of maximum tissue compression obtained with each loading level was mean 40% strain (range 31-49%) for the Low Load group, mean 67% strain (range 44%-77%) for the Moderate Load group, mean 72% strain (range 62-80%) for the High Load (undamaged) and mean 83% strain (range 74-89%) for the High Load (damaged). Four explants each were tested at the three stress levels. Explants taken from adjacent cartilage were selected as paired non-loaded controls (total 12) to control for differences in site of origin.

Glycosaminoglycan release assay. To estimate GAG depletion and release, the concentration of sulfated glycosaminoglycans was measured using 1,9-Dimethylene Blue (DMMB) as a monitor of spectrophotometric changes which occur during the formation of the sulfated GAG dye complex (Fardale, et al. (1986) *Biochim. Biophys. Acts.* 883, 173-177, Goldberg, et al. (1993) *Agents Actions* 39 Spec No, C163-C165). For GAG content measurement, samples were digested in papain and collagenase and the concentration of sulfated GAG measured using DMMB. To generate a standard curve, chondroitin-6-sulfate (Sigma, St. Louis, Mo.) was used at concentrations between 1 and 200 µg/ml. GAG released in media was normalized to the pooled mean GAG content of Control (uninjured) cartilage explants and expressed as a percentage of total GAG content.

Time Response.

To establish the time response after injury, control and loaded explants (Moderate Load) were cultured for 2, 4, 8, 24 and 48 hours. Percent chondrocytes demonstrating apoptosis and GAG release in media were measured at the end of each culture period.

Apoptosis detection.

To determine if cell death occurred in the form of apoptosis in response to mechanical injury, the same three stress levels were selected: Low Load (7 MPa), Moderate Load (14 MPa) and High Load (23 MPa). Three separate experiments were performed with explants from six different bovine joints. In a single experiment, four explants each were tested at the three stress levels. Explants taken from adjacent cartilage were selected as paired unloaded controls to control for difference sin site of origin. Two more explants were treated with 1 mM sodium nitroprusside (SNP) to serve as positive controls for induction of apoptosis (Blanco, et al. (1995) *Am. J. Pathol.* 146, 75-85). Explants were loaded as described above and fixed in 10% buffered formalin 48 hours after loading. In situ detection of apoptosis was performed on 5 µm thick sections using MEBSTAIN Apoptosis Kit (MBL, Nagoya, Japan). This uses fluorescein-dUTP to label DNA strand breaks (TUNEL method) and hence allows direct detection of DNA fragmentation. TUNEL positive cells emit a bright green fluorescence while TUNEL negative cells display an orange color due to propidium iodide counterstaining. For each explant, two histologic cross-sections taken completely across the explant were examined. Cells in all areas were counted and divided into TUNEL positive or TUNEL negative. TUNEL positive cells seen adjacent to the cut edges of the explant were not included in the analysis since these were thought to be due to the surgical trauma at harvest. Since propidium iodide would stain all cells in the fixed section, the extent of apoptosis could be quantified by counting the number of TUNEL positive relative to TUNEL negative cells. This was expressed as a percentage of all cells in the explant that exhibited TUNEL positive fluorescence. To serve as a confirmatory test, several control and loaded explants were divided into two halves. One half underwent fluorescein-dUTP labeling as described above. The other half was fixed in 2.5% glutaraldehyde buffered with 0.1M cacodylate (pH 7.2), rinsed in cacodylate buffer, postfixed for 1 hour in 2% $OsO_4$ buffered with cacodylate, dehydrated in a graded ethanol series, and embedded in Polybed 812 (Polysciences, Warrington, Pa.). Thin sections were stained with uranyl acetate and lead citrate and examined under electron microscopy for features of apoptosis.

Inhibition of Apoptosis.

To determine whether apoptosis could be prevented by caspase inhibition, 12 explants were loaded at 23 MPa (High Load) and cultured for 48 hours. For six of these explants, the media treated with z-VAD.fmk (100 µM). z-VAD.fmk is a cell-permeable fluoromethylketone peptide inhibitor of caspases and has been shown to be a broad spectrum apoptosis inhibitor in a variety of cell types (Katsikis, et al. (1997) *J. Exp. Med.* 186, 1365-1372, Slee, et al. (1996) *Biochem. J.* 315, 21-24). Six more explants were used as non-loaded controls. Percent apoptosis and GAG release in media was measured as described above.

EXAMPLE 2

Human Cartilage Studies

Cartilage explants.

Macroscopically normal tibial and femoral articular surfaces were selected from human cadaver donors between 18 and 45 years of age. Using sterile techniques, full thickness cartilage was separated from underlying subchondral bone with a scalpel. 5 mm diameter cylindrical explants, ranging from 2 to 2.8 mm in thickness, cored out using a dermal punch (Acuderm, Inc., Ft. Lauderdale, Fla.). Explants taken from adjacent sites were used as matched controls for each group in each experiment to minimize variation in cartilage response due to differences in thickness and location within the joint. Each explant was weighed and allowed to stabilize at 37° C. and 5% $CO_2$ for 48 hours in Dulbecco's modified Eagle's medium (DMEM) supplemented with 5% fetal bovine serum (FBS), L-glutamine, antibiotics and 50 mg/ml ascorbic acid.

Loading Apparatus and Procedure.

An Instron 8511 servohydraulic testing machine (Instron Corporation, Boston, Mass.) was used to mechanically load the cartilage explants. Explants were transported from the incubator to the Instron machine in sealed cell culture dishes. The total time duration of loading for a single experiment varied from approximately 1 to 2 hours depending on the number of samples. During this time, explants were maintained at 37° C. The explant was centralized on a stainless steel loading platform and a radially unconfined compressive load was applied through an impermeable stainless steel platen. Explants were subjected to a single 500 msec trapezoidal loading waveform at the selected stress (14 MPa) or strain level (30%). This loading protocol was chosen to simulate an impact injury and had been found to consistently produce between 20 and 40% apoptosis in pilot tests with bovine cartilage samples. Control explants were placed in the machine but not loaded. Both control and loaded explants were re-cultured in fresh culture media immediately after loading. Stress and strain data were recorded during the test.

Response to Mechanical Injury.

To establish extent of tissue response to mechanical injury one stress level of 14 MPa was selected. Prior pilot tests demonstrated that loads below 7 MPa did not result in any measurable cell death and loads above 20 MPa resulted in extensive structural damage of the tissue. Eight explants each taken from three donor tibial condyles were tested at this stress level. Explants taken from adjacent cartilage were selected as paired non-loaded controls to control for differences in site of origin. Explants were examined 96 hours after loading for apoptosis.

Time Response.

To establish the time response after injury, explants were loaded at 30% strain and cultured for 3, 6, 12, 24, 48 and 96 hours, and 24, 48, 96 and 168 hours after injury in separate experiments. Due to the variation in thickness and material properties of cartilage taken from different locations within the same joint, strain controlled experiments were performed as they were found to produce more consistent injury. Percent apoptosis and GAG release was measured at the end of each culture period.

Caspase Inhibition.

To determine whether caspase inhibitors could prevent apoptosis, explants were cultured in 100 mM z-VAD.fmk (a broad spectrum caspase inhibitor) immediately after injury (30% strain level). Percentage apoptosis was measured at 96 hours post-injury in three groups (control, loaded, and loaded with z-VAD.fmk) with ten explants each in two separate experiments.

Caspase Inhibition.

The presence of a time delay in the establishment of apoptosis suggests potential for agents that may inhibit this response after mechanical injury. Although apoptosis can be induced by via two major pathways (via death receptors or mitochondria), overlaps exist in the sequential activation of caspases 3, 6 and 7. Several studies have demonstrated the efficacy of caspase inhibition in preventing apoptosis in a variety of settings. Mechanically induced apoptosis can also be reduced by caspase inhibition. Explants cultured in z-VAD.fmk demonstrated a mean 50% reduction in apoptotic rates ($p<0.05$). These effects of caspase inhibition support the above findings of apoptosis detected by TUNEL, since cells undergoing necrosis cannot be rescued by caspase inhibition. In addition, it suggests that cells that are triggered to undergo apoptosis can be rescued, opening possibilities for enhancing cartilage repair by increasing or maintaining cell viability.

Glycosaminoglycan Release Assay.

To measure glycosaminoglycan release, the concentration of sulfated glycosaminoglycans (GAG) in culture media was measured using 1,9-Dimethylene Blue as a monitor of spectrophotometric changes which occur during the formation of the sulfated GAG dye complex. To generate a standard curve, chondroitin-6-sulfate (Sigma, St. Louis, Mo.) was used at concentrations between 1 and 200 mg/ml. GAG release was expressed as percent GAG content of control explants.

Apoptosis Detection.

Explants loaded as described above were fixed in 10% buffered formalin. In situ detection of apoptosis was performed on 5 mm thick sections using MEBSTAIN Apoptosis Kit (MBL, Nagoya, Japan). This uses fluorescein-dUTP to label DNA strand breaks (TUNEL method) and hence allows direct detection of DNA fragmentation. Cells demonstrating apoptosis emit a bright green fluorescence while normal cells display an orange color due to propidium iodide counterstaining. Apoptosis was quantified by counting the number of cells demonstrating apoptosis and was expressed as a percentage of the total number of cells. For further confirmation of apoptosis, several control and loaded explants were divided into two halves. One half underwent fluorescein-dUTP labeling as described above. The other half was fixed in 2.5% glutaraldehyde buffered with 0.1M cacodylate (pH 7.2), rinsed in cacodylate buffer, postfixed for 1 hour in 2% $OSO_4$ buffered with cacodylate, dehydrated in a graded ethanol series, and embedded in Polybed 812 (Polysciences, Warrington, Pa.). Thin sections were stained with uranyl acetate and lead citrate and examined under electron microscopy for features of apoptosis. In addition, representative histologic sections were examined for presence of a caspase cleavage site in cytokeratin 18 that exposes a neo-epitope specific for apoptosis. This was detected by immunohistochemical staining with M30 (Cytodeath, Boehringer Mannheim, Eugene, Oreg.), a monoclonal antibody that recognizes the neo-epitope exposed in early apoptosis.

EXAMPLE 3

Additional Studies

Chondrocyte Apoptosis After Mechanical Injury to Bovine Cartilage.

To address the form of cell death after mechanical injury, full thickness cartilage explants from the normal weight-bearing portions of mature bovine femoral condyles were selected. Explants from adjacent sites were used as matched controls for each group in each experiment to minimize variation in cartilage response due to difference in thickness and location within the joint. An Instron 8511 servohydraulic testing machine was used to mechanically load the cartilage explants. To establish extent of mechanical injury three stress levels were selected: low load (7 MPa), moderate load (14 MPa) and high load (23 MPa). Prior tests had demonstrated that loads below 7 MPa did not result in any detectable cell death and loads above 23 MPa resulted in extensive structural damage of the tissue. In each experiment, four explants each were tested at the three stress levels. The range of maximum tissue compression obtained with each loading level was mean 40% strain (range 31-49%) for the low load group, mean 67% strain (range 44-77%) for the moderate load group and 83% strain (range 74-89%) for the high load group. The explants were cultured for 48 h after loading and apoptosis was assessed by TUNEL. The low load explants did not show any significant difference in apoptosis rate as compared to the unloaded controls. Both moderate and high load explants exhibited significantly higher apoptosis rates at 40% and 47%, respectively ($p<0.05$) (Table 2).

TABLE 2

Load-induced apoptosis in human, bovine and rabbit cartilage

| Type of explant | Source | Ctr | Load |
|---|---|---|---|
| Full thickness cartilage | Bovine femoral (n = 20) | 7 (0.7) | 43 (7.5) |
| Full thickness cartilage | Human femoral/tibial (n = 8) | 11 (3.1) | 32 (9.6) |
| Full thickness cartilage | Human tali (n = 10) | 12 (7.1) | 26 (8.2) |
| Osteochondral | Rabbit patellae (n = 4) | 1 (2.1) | 15 (4.3) |
| Osteochondral | Human patellae (n = 4) | 3 (0.9) | 17 (7.9) |

Full thickness cartilage = 5 mm diameter explants
Osteochondral = whole patella

The control explants demonstrated a small number of apoptotic cells, mainly located in the superficial zone. The high load explants contained apoptotic cells predominantly in the superficial and intermediate zones in various stages of apoptosis, including chromatin condensation, cell shrinkage and the formation of blebs at the cell membrane. Associated with this is the accumulation of apoptotic bodies in the extracellular matrix adjacent to apoptotic cells. A small percentage of cells with abnormal morphology (<5%) had necrotic appearance on electron microscopy.

Release of sulfated glycosaminoglycans (GAG) was analyzed as a measure of the extent of damage sustained by the explant. GAG release increased with intensity of loading within the range tested at 48 hours after loading. There was no significant difference between the unloaded and the low load samples. Moderate and high load explants released significantly higher levels of GAG than the unloaded controls ($p<0.02$). GAG depletion was assessed by dimethylene blue binding assays of the culture supernatants and this correlated with the reduced of safranin O staining of the cartilage sections.

The next set of experiments determined whether load-induced apoptosis was sensitive to pharmacologic manipulation and whether inhibition of apoptosis was associated with reduced GAG depletion. The broad-spectrum caspase inhibitor z-VAD.fmk caused a >50% reduction in the apoptosis rate of the high and intermediate load groups (Table 3). Associated with the reduction in apoptosis was a normalization of the GAG depletion.

TABLE 3

Pharmacologic modulation of apoptosis after cartilage injury in vitro

| Source | Agent | Control | Loaded | Loaded + Agent |
|---|---|---|---|---|
| Bovine | z-VAD.fmk | 16 (±8.4) | 65 (±13.2)* | 31 (±13.9)* |
| Bovine | IGF-1 | 10 (±3.3) | 61 (±12.8)* | 42 (±10.9)* |
| Bovine | Dexameth. | Same as above | Same as above | 47 (±11.2)* |
| Human | z-VAD.fmk | 9 (±4.5) | 44 (±9.9)* | 34 (±10.2)* |
| Human | IGF-1 | 3 (±3.3) | 17 (±5.7)** | 10 (±6.2)** |

Bovine (femoral condyles) and Human cartilage (femoral condyles and tibial plateaus)
*Loaded at 23 MPa; **Loaded at 30% strain
Two loading protocols: Stress controlled (23 MPa); Strain controlled (30% strain)
Sample size: n = 8 to 10 in each group
Mean (±SD) apoptosis rates in different groups Intraarticular Injection of Caspase Inhibitor in Rabbits with Ligament Transection.

A pilot study was performed to assess feasibility and efficacy of caspase inhibition in vivo. Eight New Zealand White rabbits were divided into anterior cruciate ligament transection (ACLT) and ACLT+caspase inhibitor (CI) groups. Both groups underwent bilateral ACLT. The ACLT+CI group was treated with intra-articular injections of 25 μg of z-VAD.fmk three times per week for six weeks while the control group received saline injections. Rabbits were euthanised at six weeks and femoral and tibial articular cartilage evaluated by India ink staining and histologic Mankin grading after Safranin-O stain.

Under India ink examination, all the ACLT rabbits demonstrated cartilage lesions on both femoral condyles, lateral tibial condyles and posteromedial tibial condyles, ranging from grade III (overt fibrillation) to grade IVa (erosions >5 mm). The ACLT+CI rabbits demonstrated lesions that were smaller in area. The grade ranged from II (minimum fibrillation), with only one rabbit (two knees) having a Grade III to IVa lesion. Histologically, more knees from the ACLT group had higher Mankin scores. 87% (⅞) ACLT knees had grades 5 or higher, while 50% (⅘) ACLT+CI knees were graded 5 or higher. The India ink stained femoral condyles were photographed and digital images were used to quantify the surface areas of the lesions. This revealed that caspase inhibitor injection reduced the size of the cartilage lesions by ~80%.

Chondrocyte Apoptosis After Mechanical Injury to Human Cartilage.

In an additional study the apoptosis response of human articular cartilage to mechanical stress was examined. Full thickness human cartilage explants, 5 mm in diameter were subjected to a single static mechanical stress of 14 MPa for 500 msec under radially unconfined compression. GAG release and percentage of cells undergoing apoptosis were measured at 96 hours after injury. To establish the time course of apoptosis, explants were subjected to 30% strain and cultured for varying intervals up to 7 days after injury. A group of loaded explants were also treated with the broad spectrum caspase inhibitor z-VAD.fmk after injury. Mean chondrocyte apoptosis of 34% (SD±11) was observed at 96 hours in response to mechanical loading at 14 MPa, compared to 4% (SD±2) in the non-loaded explants. GAG release was also higher for the loaded explants, mean 1.9%, (SD±0.14) of total GAG content, compared to control explants, mean 0.8%, (SD±0.28). The percentage of apoptotic cells also correlated with the level of GAG release into the culture media. The percentage of apoptotic chondrocytes demonstrated a progressive increase from 6 hours to 7 days post-injury. When loaded explants were cultured in z-VAD.fmk after injury, a 50% reduction in apoptosis rates was seen. Thus, the apoptosis response of human cartilage to mechanical stress is similar to that seen with bovine tissue.

What is claimed is:

1. A process of inhibiting apoptotic cell death in injured cartilage following traumatic mechanical injury of the cartilage of a human patient, comprising:
   a. identifying a human patient having a traumatic mechanical injury to cartilage; and
   b. inhibiting the activity of cysteine-aspartate-specific proteases in the injured cartilage within seven days of the injury by administering to the patient a sufficient amount of a fluoromethylketone caspase inhibitor to achieve a concentration of inhibitor in an interstitial fluid which perfuses the injured cartilage of from about 20 µM to about 250 µM, wherein the fluoromethylketone caspase inhibitor is administered by an intra-articular injection.

2. The process of claim 1 wherein the fluoromethylketone caspase inhibitor is benzyloxycarbonyl-Val-Ala-Asp (OMe) fluoromethylketone.

3. A process of inhibiting glycosaminoglycan release from cartilage following mechanical injury of the cartilage, comprising inhibiting apoptotic cell death in human injured cartilage by contacting the injured cartilage with an effective amount of a fluoromethylketone caspase inhibitor that is a cysteine-aspartate-specific-protease within seven days of traumatic mechanical injury to the cartilage thereby inhibiting glycosaminoglycan release from the cartilage, wherein the fluoromethylketone caspase inhibitor is injected into intra-articular space to achieve a concentration of fluoromethylketone caspase inhibitor in an interstitial fluid which perfuses the injured cartilage of from about 20 µM to about 250 µM.

4. The process of claim 3 wherein the fluoromethylketone caspase inhibitor is benzyloxycarbonyl-Val-Ala-Asp (OMe) fluoromethylketone.

5. The process of claim 1 or 3 wherein the traumatic mechanical injury of the cartilage is blunt traumatic mechanical injury.

6. The process of claim 1 or 3 wherein the traumatic mechanical injury of the cartilage is external traumatic mechanical injury.

7. The process of claim 1, wherein the cartilage is articular cartilage.

8. The process of claim 3, wherein the cartilage is articular cartilage.

* * * * *

UNITED STATES PATENT AND TRADEMARK OFFICE
CERTIFICATE OF CORRECTION

PATENT NO. : 7,411,000 B2
APPLICATION NO. : 10/099408
DATED : August 12, 2008
INVENTOR(S) : D'Lima et al.

Page 1 of 1

It is certified that error appears in the above-identified patent and that said Letters Patent is hereby corrected as shown below:

In the specification,

Column 1, line 14, should read as follows:

This invention was made with government support under AG007996 awarded by the National Institutes of Health. The government has certain rights in the invention.

Signed and Sealed this
Twenty-third Day of February, 2016

Michelle K. Lee
*Director of the United States Patent and Trademark Office*